(12) United States Patent
Waki

(10) Patent No.: US 7,766,836 B2
(45) Date of Patent: Aug. 3, 2010

(54) ULTRASOUND DIAGNOSTIC APPARATUS, PROGRAM FOR IMAGING AN ULTRASONOGRAM, AND METHOD FOR IMAGING AN ULTRASONOGRAM

(75) Inventor: Koji Waki, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 394 days.

(21) Appl. No.: 11/813,291

(22) PCT Filed: Dec. 27, 2005

(86) PCT No.: PCT/JP2005/023886
§ 371 (c)(1),
(2), (4) Date: Jul. 3, 2007

(87) PCT Pub. No.: WO2006/073088
PCT Pub. Date: Jul. 13, 2006

(65) Prior Publication Data
US 2008/0081993 A1    Apr. 3, 2008

(30) Foreign Application Priority Data
Jan. 4, 2005    (JP) .......................... 2005-000257

(51) Int. Cl.
*A61B 8/00*    (2006.01)
(52) U.S. Cl. ...................................... 600/443; 600/438
(58) Field of Classification Search .............. 600/437, 600/438, 439, 443
See application file for complete search history.

(56) References Cited
U.S. PATENT DOCUMENTS
5,495,771 A    3/1996    Sumi et al.
6,048,317 A    4/2000    Langguth
6,508,768 B1 *    1/2003    Hall et al. ................. 600/443
2004/0034304 A1    2/2004    Sumi et al.

FOREIGN PATENT DOCUMENTS
EP    0 842 638    5/1998

(Continued)

OTHER PUBLICATIONS

European Office Action issued in corresponding European Patent Application No. 05 822 712.5, dated Dec. 23, 2009.

*Primary Examiner*—Eric F Winakur
*Assistant Examiner*—Michael T Rozanski
(74) *Attorney, Agent, or Firm*—Antonelli, Terry, Stout & Kraus, LLP.

(57) ABSTRACT

An ultrasound diagnostic apparatus includes a probe 102 that transmits and receives ultrasound waves to/from a subject, transmitting means 120 for supplying a drive signal to the probe 102 for transmitting ultrasound waves, receiving means 122 for receiving and processing a signal output from the probe 102, a displacement calculating unit 105 for measuring displacement of a tissue according to an output signal from an ultrasound transmitting and receiving unit 103, a color DSC 108 for reconstructuring an elasticity image on the basis of the displacement of the tissue, and an image display 112 for displaying the elasticity image. Further, the ultrasound diagnostic apparatus includes setting means 113B for setting a displacement search direction that sets a search direction of the displacement to match a tissue displacement direction for displacing the tissue. The color DSC 108 constructures the elasticity image on the basis of the measurement value of the displacement search direction.

23 Claims, 11 Drawing Sheets

FOREIGN PATENT DOCUMENTS

| | | |
|---|---|---|
| EP | 1 123 687 | 8/2001 |
| EP | 1 123 687 A2 | 8/2001 |
| JP | 2000-060853 | 2/2000 |
| JP | 2000-271117 | 10/2000 |
| JP | 2004-351062 | 12/2004 |

* cited by examiner

FIG.6
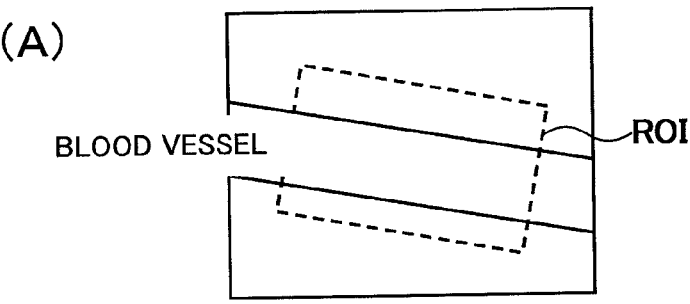
(A) BLOOD VESSEL — ROI
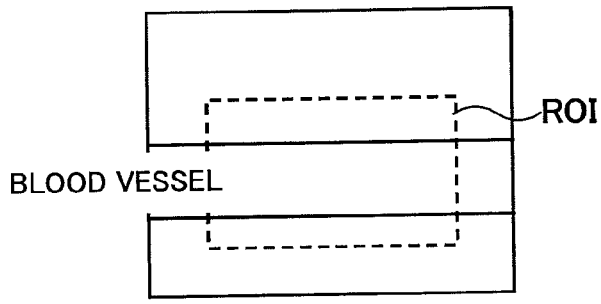
(B) BLOOD VESSEL — ROI
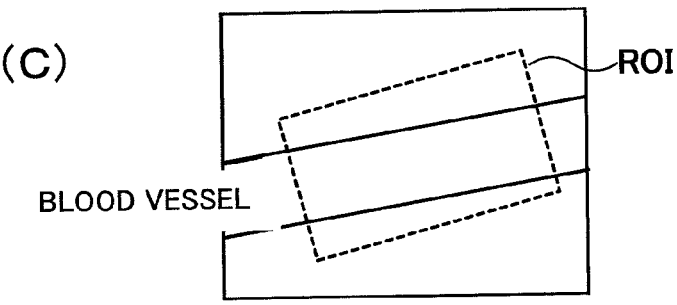
(C) BLOOD VESSEL — ROI
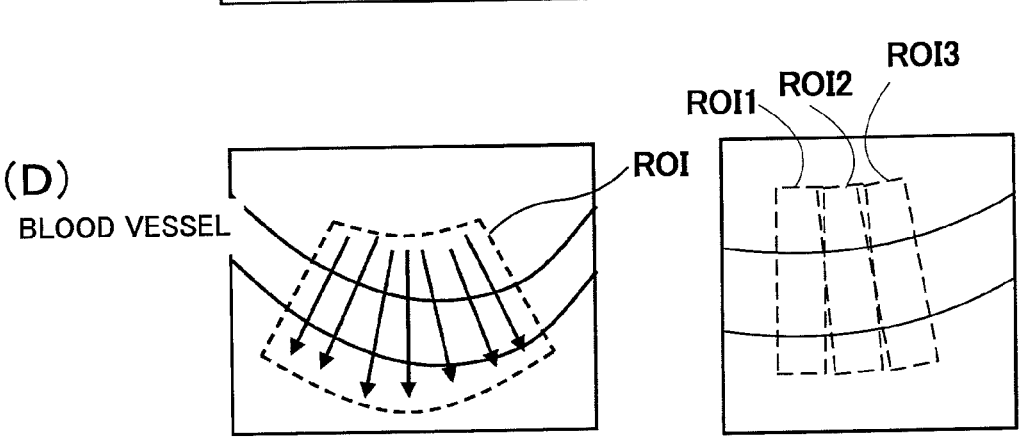
(D) BLOOD VESSEL — ROI    ROI1 ROI2 ROI3

(1) LONGITUDINAL 8mm
    LATERAL      1mm    $\alpha = \cos(-1)1 = 0°$ (2) LONGITUDINAL 0mm
    LATERAL      1mm    $\alpha = \cos(-1)0 = 90°$ (3) LONGITUDINAL 8mm
    LATERAL      8mm    $\alpha = \cos(-1)1/\sqrt{2} = 45°$ FIG.9
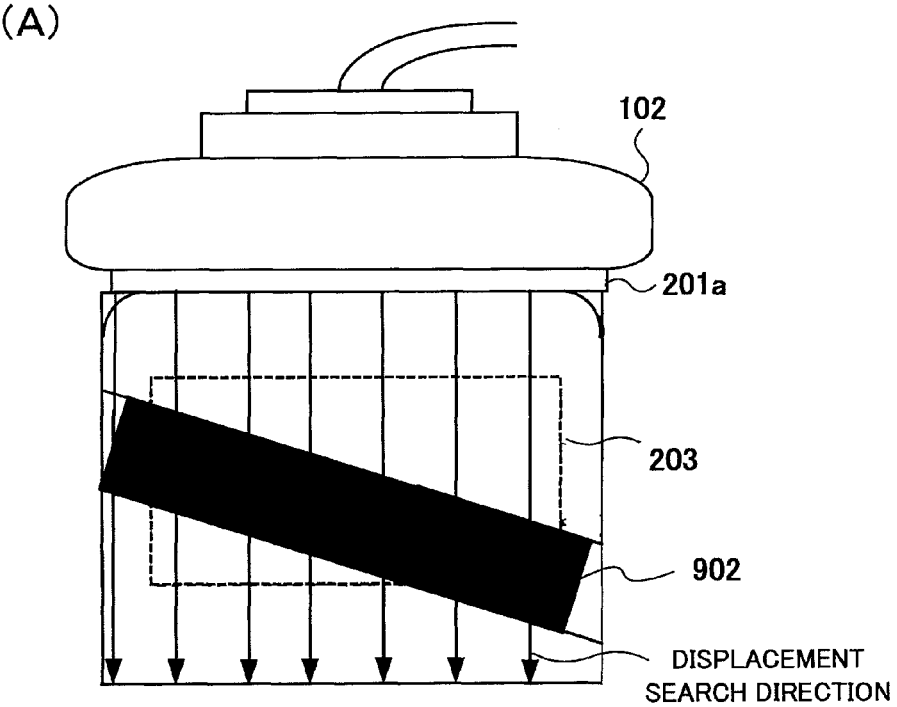
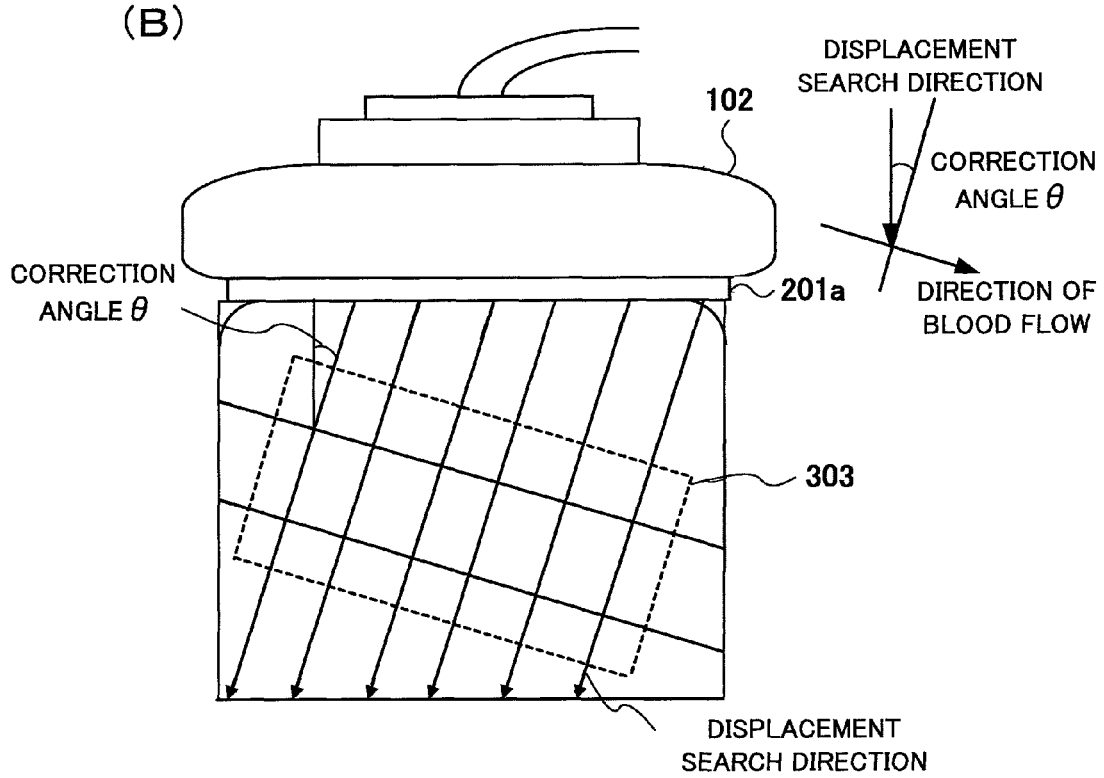

ULTRASOUND DIAGNOSTIC APPARATUS, PROGRAM FOR IMAGING AN ULTRASONOGRAM, AND METHOD FOR IMAGING AN ULTRASONOGRAM

TECHNICAL FIELD

The present invention relates to a technology for imaging an ultrasonogram that is an elasticity image indicating characteristics such as strain or hardness of the living tissue of a subject.

BACKGROUND ART

An ultrasound diagnostic apparatus for imaging an ultrasonogram comprises that supplying a drive signal to an ultrasound probe for transmitting ultrasound waves to a subject, receiving a reflection echo generated from the subject to the ultrasound probe, and reconstructuring and displaying the ultrasonogram on the basis of the reflection echo output from the ultrasound probe.

One of the ultrasound diagnostic apparatuses is well known to take an elasticity image indicating characteristics such as strain or hardness of a living tissue of the subject. For example, the ultrasound diagnostic apparatus captures images on time series on the living tissue upon applying pressure to the subject, measures the displacement of the living tissue with the correlation with the captured images on time series, obtains elasticity data (e.g., strain and modulus of elasticity) on the basis of the measured displacement, and reconstructs an elasticity image.

As methods for applying pressure to the subject upon measuring the displacement of the living body, there are a method for using a body motion, as a pressure source, for periodically pressurizing the organ (e.g., vasculitic pulsation), a method for pressurizing an ultrasound probe to the subject by manually pressing the ultrasound probe to the subject, and a method for pressurizing the subject by using a transducer (e.g., Patent Document JP 2000-60853 A1).

The prior arts including those disclosed in the Patent Document do not substantially consider a relationship between the direction (hereinafter, referred to as a tissue displacement direction) for actually displacing the living tissue upon applying pressure to the subject and an elasticity calculating direction (hereinafter, referred to as displacement search direction) for measuring the displacement of the living tissue. That is, the conventional displacement-search direction is fixedly set to an ultrasound transmitting and receiving surface in the vertical direction. On the other hand, the tissue displacement direction fluidly changes due to the pressurizing direction and the shape of a pressuring surface to the living tissue. Therefore, upon measuring the displacement of the living tissue, the displacement search direction does not match the tissue displacement direction. In this case, there is concern that a measurement value includes an error due to the displacement. When an elasticity image is reconstructed on the basis of the measurement value, the elasticity image cannot precisely indicate characteristics of the living tissue.

DISCLOSURE OF INVENTION

It is an object of the present invention to provide an ultrasound diagnostic apparatus, program for imaging an ultrasonogram, and method for imaging an ultrasonogram that are suitable to take an elasticity image precisely indicating characteristics of the living tissue by improving measurement precision of the displacement of the living tissue.

In order to achieve the object, an ultrasound diagnostic apparatus according to the present invention comprises: an ultrasound probe for transmitting and receiving ultrasound waves to/from a subject; means for supplying a drive signal to the ultrasound probe transmitting the ultrasound waves to the subject; means for receiving and processing a signal output from the ultrasound probe; means for reconstructing an elasticity-image on the basis of displacement of the tissue measured from an output signal from the receiving means; and means for displaying the elasticity image; wherein further comprising: means for setting displacement search direction to match a tissue displacement direction of the displacement of the tissue; wherein the means for reconstructing the elasticity-image measures the displacement of the search direction and constructures the elasticity image.

According to a preferable aspect of the present invention, even if the displacement search direction does not match the tissue displacement direction, the displacement search direction can match the tissue displacement direction. The displacement of the tissue is measured in the displacement search direction, thereby measuring the displacement in the direction for actually displacing the tissue. As a consequence, the precision of a measurement value is improved. The elasticity image is constructed on the basis of the measurement value, thereby reducing artifact caused in the elasticity image. Thus, the elasticity image is obtained with high quality for precisely indicating the characteristics such as the strain or hardness of the tissue.

Further, program for imaging an ultrasonogram according to the present invention enables a control computer to execute: a setting process of a displacement search direction to match a tissue displacement direction for displacing the tissue of a subject; a supplying process for supplying a drive signal to the ultrasound probe that transmits the ultrasound waves to the subject; a receiving process for receiving and processing a signal output from the ultrasound probe; a measuring process for measuring a displacement of the search direction from the received signal processed by the receiving procedure; a reconstructing process for reconstructing an elasticity image on the basis of the measurement value of the displacement; and a displaying process for displaying the elasticity image.

Furthermore, a method for imaging an ultrasound imaging comprises: a setting step for setting a displacement search direction to match a tissue displacement direction of a living tissue of a subject; a supplying step for supplying a drive signal to an ultrasound probe that transmits and receives ultrasound waves to/from the subject; a receiving step for receiving and processing a signal output from the ultrasound probe; a measuring step for measuring the displacement along the set search direction of the living tissue from a signal processed by the processing step; a reconstructing step for reconstructing an elasticity image on the basis of the measurement value of the displacement; and a displaying step for displaying the elasticity image.

BRIEF DESCRIPTION OF THE DRAWINGS

FIG. 6 is a diagram showing a setting example of a region of interest in various vascular channels.

FIG. 9 is a diagram showing another processing for automatically detecting the tissue displacement direction.

BEST MODE FOR CARRYING OUT THE INVENTION

Figure 1:
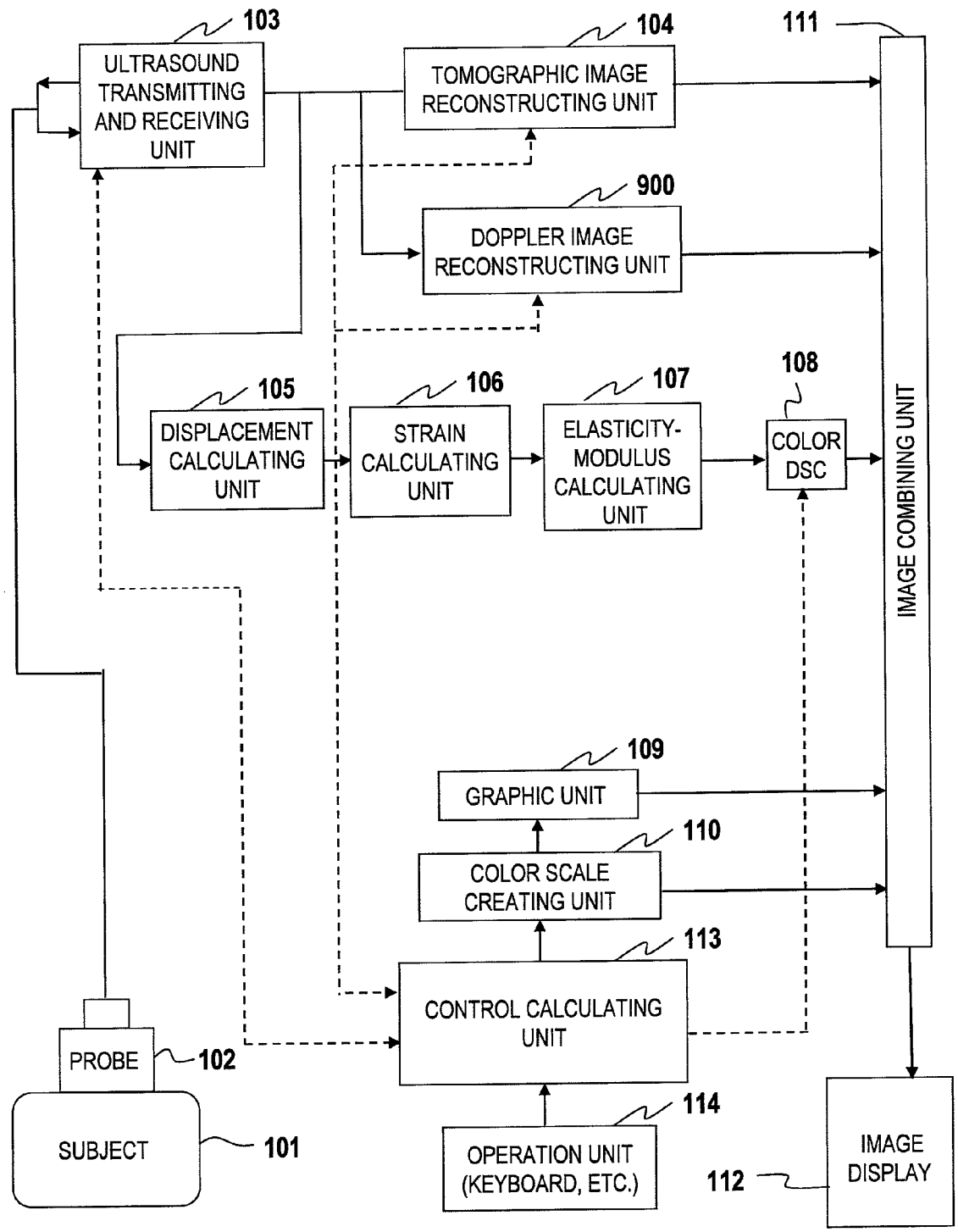
FIG. 1 is a block diagram showing the structure of an ultrasound diagnostic apparatus according to one embodiment of the present invention.
Figure 2:
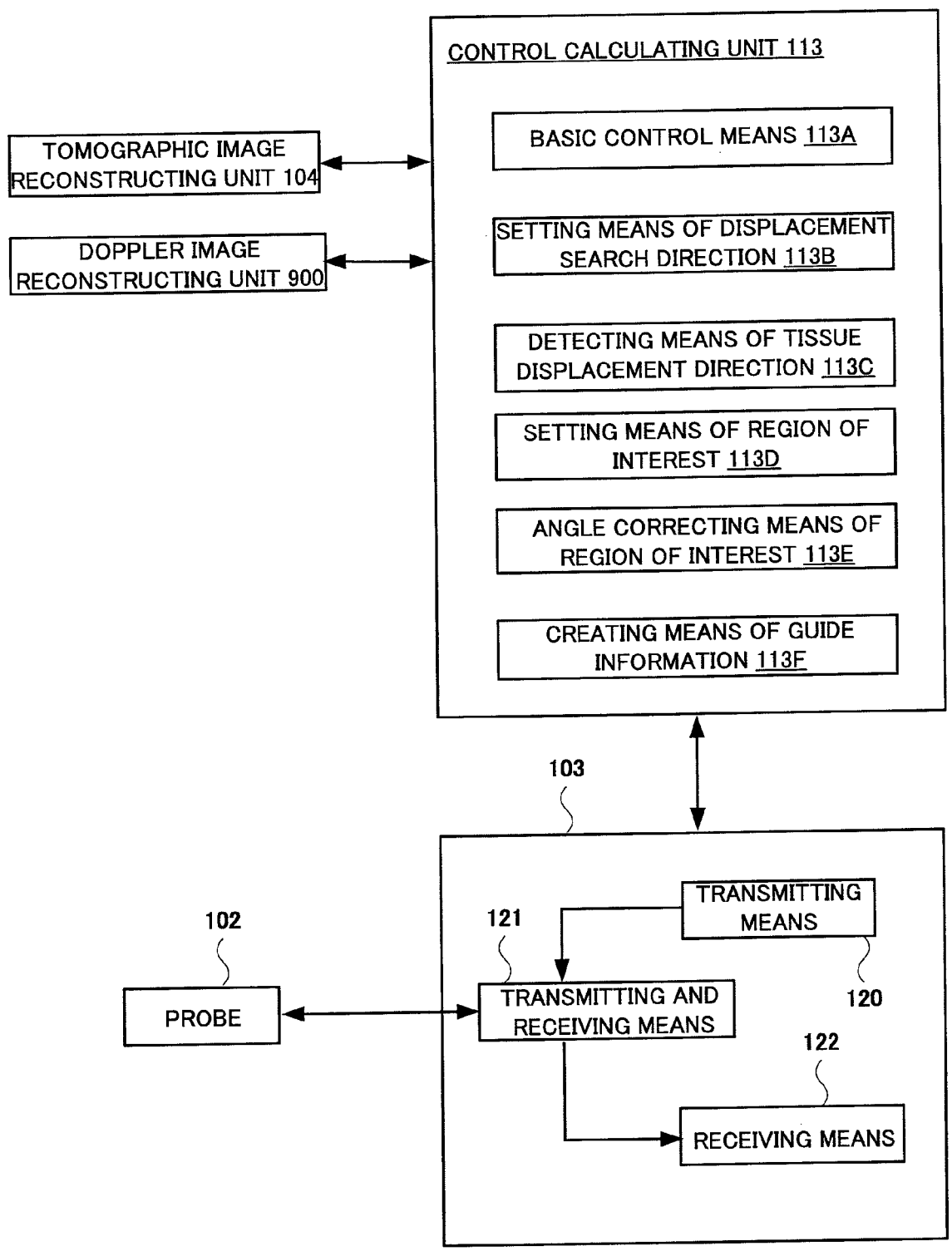
FIG. 2 is a diagram showing the structure of a control calculating unit shown in FIG. 1.

Hereinbelow, a description will be given of an ultrasound diagnostic apparatus and a method for imaging an ultrasonogram according to embodiments of the present invention with reference to the drawings. FIG. 1 is a block diagram showing the structure of the ultrasound diagnostic apparatus according to one embodiment of the present invention. FIG. 2 is a diagram showing the structure of a control calculating unit shown in FIG. 1.

Referring to FIGS. 1 and 2, the ultrasound diagnostic apparatus comprises: an ultrasound probe (hereinafter, referred to as a probe 102) that transmits and receives ultrasound waves to/from a subject 101; an ultrasound transmitting and receiving unit 103 that supplies a transmitting drive signal to the probe 102 and processes a received signal output from the probe 102; elasticity-image reconstructing means that constructures an elasticity image on the basis of the displacement of the living tissue measured from the output signal from the ultrasound transmitting and receiving unit 103; and an image display 112, as display means, which displays the elasticity image. Herein, the elasticity-image reconstructing means comprises: a displacement calculating unit 105; a strain calculating unit 106; a modulus-of-elasticity calculating unit 107; and a color digital scanning converter 108 (hereinafter, color DSC 108). Further, the elasticity-image reconstructing means comprises a control calculating unit 113 that outputs a control command to the ultrasound transmitting and receiving unit 103 and the elasticity-image reconstructing means.

Further, referring to FIG. 2, setting means 113B in a displacement search direction is mounted on the control calculating unit 113 applied to the ultrasound diagnostic apparatus according to the embodiment. The setting means 113B of the displacement search direction sets, upon imaging an elasticity image, an elasticity calculating direction (hereinafter, referred to as a displacement search direction) for measuring the displacement of the living tissue of the subject 101 to match a direction (hereinafter, referred to as a tissue displacement direction) for actually displacing the living tissue. Subsequently, the setting means 113B of the displacement search direction allows the elasticity-image reconstructing means to measure the displacement of the living tissue in the set displacement search direction.

As a consequence, even if the displacement search direction does not match the tissue displacement direction, the displacement search direction can match the tissue displacement direction. Therefore, the displacement along the direction for actually displacing the living tissue is measured, thereby improving the precision of a measurement value. The elasticity image is constructed on the basis of the measurement value, thereby precisely indicating the characteristics of the living tissue on the elasticity image.

More specifically, the ultrasound diagnostic apparatus according to the embodiment will be described. The ultrasound diagnostic apparatus mainly comprises an ultrasound transmitting and receiving system, a tomographic image imaging system, an elasticity-image imaging system, a display system, and a control system.

The ultrasound transmitting and receiving system comprises the probe 102 and the ultrasound transmitting and receiving unit 103. The probe 102 has an ultrasound transmitting and receiving surface that transmits and receives ultrasound waves to/from the subject 101 by mechanical or electrical beam scanning. On the ultrasound transmitting and receiving surface, a plurality of transducers are arranged. The transducers mutually convert electrical signals and ultrasound waves. Further, the probe 102 has a pressure sensor on the ultrasound transmitting and receiving surface. The pressure sensor detects pressure applied to the ultrasound transmitting and receiving surface and outputs the detected pressure to a pressure measuring unit. The pressure measuring unit outputs pressure data to the strain calculating unit 106 and the modulus-of-elasticity calculating unit 107.

Referring to FIG. 2, the ultrasound transmitting and receiving unit 103 comprises transmitting means 120 that supplies a drive signal (pulse) via transmitting and receiving means 121 to the probe 102; and receiving means 122 that processes a received signal from the probe 102 via the transmitting and receiving means 121.

The transmitting means 120 in the ultrasound transmitting and receiving unit 103 has a circuit for transmitting pulses as drive signals that drive transducers of the probe 102 and generate ultrasound waves, and a circuit for setting the depth of a convergence point of ultrasound beams emitted from the probe 102. Herein, the transmitting means 120 according to the embodiment selects the transducer for supplying the pulses via the transmitting and receiving means 121, and controls a generation timing of the transmitting pulses so as to perform the scanning in the tissue displacement direction with ultrasound beams sent from the probe 102. That is, the transmitting means 120 controls a delay time of the pulse signals, thereby controlling the scanning direction of ultrasound beams.

The receiving means 122 in the ultrasound transmitting and receiving unit 103 has a circuit that amplifies signals output from the probe 102 via the transmitting and receiving means 121 and generates an RF signal, i.e., received echo signal, and a circuit that shapes and adds the phase of the RF signal and generates RF signal data on times series. The receiving means 122 supplies a predetermined delay time to the reception echo signal obtained by the ultrasound beams transmitted from the probe 102 via the transmitting and receiving means 121, and shapes and adds the matching phases.

The tomographic image imaging system comprises a tomographic image reconstructing unit 104. The tomographic image reconstructing unit 104 has a signal processing section and a monochrome scanning converter. The signal processing section constructs grayscale tomographic data (e.g., monochrome tomographic image data) of the subject 101 by performing image processing of the RF signal output from the ultrasound transmitting and receiving unit 103. Herein, the image processing includes gain correction, log compression, detection, contour emphasis, and filter processing. The monochrome scanning converter reads the tomographic data of the subject 101 stored in a frame memory on the unit basis of frame, and outputs the read tomographic data synchronously with TV. Herein, the monochrome scanning converter comprises an A/D converter that converts the tomographic data output from the signal processing section into a digital signal, a frame memory that stores a plurality of pieces of tomographic image data digitized on time series, and a controller that outputs a read command for reading the tomographic data from the frame memory.

The elasticity-image imaging system comprises the displacement calculating unit 105 that is arranged to be branched from the output terminal of the ultrasound transmitting and receiving unit 103, the strain calculating unit 106, the modulus-of-elasticity calculating unit 107, and the color DSC 108.

The displacement calculating unit 105 measures the displacement of the living tissue of the subject 101 on the basis of the RF signal data output from the ultrasound transmitting and receiving unit 103. The displacement calculating unit 105 comprises an RF signal selecting section, a calculating section, and a filter section.

The RF signal selecting section in the displacement calculating unit 105 comprises a frame memory and a selecting portion. The RF signal selecting section stores, to the frame memory, the RF signal data on time series output from the ultrasound transmitting and receiving unit 103, and the selecting portion selects one set, i.e., two pieces of RF signal frame data from among the RF signal frame data after the storage. More specifically, the RF signal selecting section sequentially ensures, to the frame memory, the RF signal data on time series output from the ultrasound transmitting and receiving unit 103 in accordance with an image frame rate. Further, the RF signal selecting section selects RF signal frame data (N) as first data from among the RF signal data stored in the frame memory in accordance with the command output from the control calculating unit 113. Subsequently, the RF signal selecting section selects RF signal frame data (X) as second data from among the RF signal data stored in the frame data in accordance with a command output from the control calculating unit 113. Herein, the RF signal frame data (X) is selected from among RF signal frame data (N-1, N-2, N-3, . . . , N-M) that was stored in the frame memory before the RF signal frame data (N). Incidentally, N, M, and X are natural numbers as index Nos. related to the RF signal frame data.

The calculating section in the displacement calculating unit 105 obtains the displacement of the living tissue along the displacement search direction on the basis of one set of the RF signal frame data. Specifically, the calculating section executes one-dimensional or two-dimensional correlation processing between the first RF signal frame data (N) and the second RF signal frame data (X) selected by the RF signal selecting section. For example, the calculating section obtains the displacement or moving vector (hereinafter, generically referred to as displacement) of the living issue in the displacement search direction corresponding to pixels of the tomographic image by applying a block matching method as the correlation processing. Herein, the moving vector means the one-dimensional or two-dimensional displacement distribution on the direction and size of the displacement. According to the block matching method, an image is divided into a block containing, e.g., N×N pixels, the block within the region of interest is focused, a block approximate to the focused block is searched from among the past frames, the search result is referred to, and prediction coding, i.e., processing for determining a sample value with the difference is performed.

Incidentally, the filter section of the displacement calculating unit 105 has a filter circuit that equalizes the displacement of the variation of the living tissue, output from the displacement calculating section, and performs pre-processing for smoothly executing the post signal-processing.

The strain calculating unit 106 calculates strain data (S=ΔL/X) of the tissue by spatially differentiating the amount of movement of the tissue, e.g., displacement ΔL of the tissue, output from the displacement calculating unit 105. Further, the modulus-of-elasticity calculating unit 107 calculates data on the modulus of elastic of the tissue by dividing the change in pressure by the change in displacement. For example, the modulus-of-elasticity calculating unit 107 obtains pressure ΔP applied to the ultrasound transmitting and receiving surface of the probe 102 from the pressure measuring section. Subsequently, the modulus-of-elasticity calculating unit 107 obtains the Young's modulus Ym (Ym=(ΔP)/(ΔL/L) as data on the modulus of elasticity on the basis of the pressure ΔP and the displacement ΔL. As mentioned above, the modulus-of-elasticity calculating unit 107 obtains the data on the modulus of elasticity corresponding to points of the tomographic image, thereby obtaining the two-dimensional elasticity image data. Incidentally, the Young's modulus means a ratio of simple tensile stress applied to a subject to strain caused in parallel with the stress. Further, the strain data and the data on the modulus of elasticity are generically referred to as elasticity data, and the elasticity data on the unit basis of frame is properly referred to as elasticity frame data.

The color DSC 108 constructs a color elasticity image of the body issue of the subject 101 on the basis of the elasticity data output from the strain calculating unit 106 or the modulus-of-elasticity calculating unit 107. For example, the color DSC 108 has an elasticity data processing portion, a color scanning converter, and a frame memory. The elasticity data processing portion stores the elasticity frame data output from the strain calculating unit 106 or the modulus-of-elasticity calculating unit 107 to the frame memory. The elasticity data processing portion performs image processing of the elasticity frame data read from the frame memory in accordance with the command output from the control calculating unit 113.

The color scanning converter in the color DSC 108 is a color tone converting unit that executes color tone converting processing of the elasticity frame data output from the elasticity data processing portion on the basis of a color map. Herein, the color map correlates the size of elasticity data with hue information determined by light's three primary colors, that is, red (R), green (G), and blue (B). Incidentally, red (R), green (G), and blue (B) have 256 tones, and as the color is closer to the 255-th tone, the image is displayed with higher luminance, and as the color is closer to the zero-th tone, the image is displayed with lower luminance.

For example, the color scanning converter in the color DSC 108 converts the color into red code when the strain data output from the elasticity data processing portion is low, and into blue code when the strain data is high, thereby storing the data to the frame memory. Further, the color scanning converter reads the elasticity frame data from the frame memory synchronously with TV in accordance with the control command, and allows the image display 112 to display the read data. Herein, in the elasticity image based on the elasticity frame data after converting the tone, a hard portion (e.g., tumor) of the tissue is drawn to a red-color system, and a peripheral portion of the hard portion is drawn to a blue-color system. This elasticity image is viewed, thereby visually grasping the wideness and size of the tumor. Incidentally, an operation unit 114 such as a keyboard is connected to the color DSC 108 via the control calculating unit 113. The color DSC 108 can change the tone of a color map in accordance with a command input via the operation unit 114.

The display system comprises a graphic unit 109, a color scale creating unit 110, an image combining unit 111, and the image display 112. The graphic unit 109 creates an image except for the tomographic image and for the elasticity image (e.g., frame work of the screen and graphical user interface). The color scale creating unit 110 creates a color scale indicating stepwise change in hue. Herein, the color scale can correspond to a color map of the color DSC 108.

The image combining unit 111 creates one ultrasonogram by combining a tomographic image output from the tomographic image reconstructing unit 104, an elasticity image output from the color DSC 108, an image output from the graphic unit 109, and a color scale output from the color scale creating unit 110. For example, the image combining unit 111 includes a frame memory, an image processing section, and an image selecting section. Herein, the frame memory stores the tomographic image output from the tomographic image reconstructing unit 104, the elasticity image output from the color DSC 108, the frame work image output from the graphic unit 109, and the color scale output from the color scale creating unit 110. The image processing section reads the tomographic image and the elasticity image from the frame memory in accordance with the control command, and adds and combines luminance information and hue information of pixels corresponding on the same coordinate system of the tomographic image and the elasticity image with a setting ratio. That is, the image processing section relatively superimposes the elasticity image on the tomographic image on the same coordinate system. The image selecting section selects the image displayed on the image display 112 from among the images stored in the frame memory in accordance with the control command. The image display 112 has a monitor that displays the image data output from the image combining unit 111.

Referring to FIG. 2, the control system comprises the control calculating unit 113 and the operation unit 114. The control calculating unit 113 comprises basic control means 113A, setting means 113B of the displacement search direction, detecting means 113C of the tissue displacement direction, setting means 113D of the region of interest, angle correcting means 113E of the region of interest, and guide information creating means 113F.

The basic control means 113A outputs various control commands to an ultrasound transmitting and receiving system, a tomographic image imaging system, an elasticity-image imaging system, and a display system. The setting means 113B of the displacement search direction resets the displacement search direction to match the tissue displacement direction when the displacement search direction does not match the tissue displacement direction. Herein, the displacement search direction is an elasticity data calculating direction as the reference upon measuring the displacement of the tissue of the subject 101. The detecting means 113C of the tissue displacement direction detects the tissue displacement direction of the tissue that is actually displaced upon applying pressure to the tissue of the subject 101. The setting means 113D of the region of interest sets the region of interest (ROI: Region Of Interest) to the tomographic image displayed on the image display 112 in accordance with the command input via the operation unit 114. The angle correcting means 113E of the region of interest corrects the setting angle of the region of interest set by the setting means 113D. The guide information creating means 113F creates guide information indicating the inclination of the probe 102 when the displacement search direction matches the tissue displacement direction and allows the image display 112 to display the created information. Incidentally, the operation unit 114 has a keyboard or point device as various setting interface.

Herein, a specific description will be given of the control calculating unit 113 according to the embodiment with reference to the drawings.

First Embodiment

Figure 3:
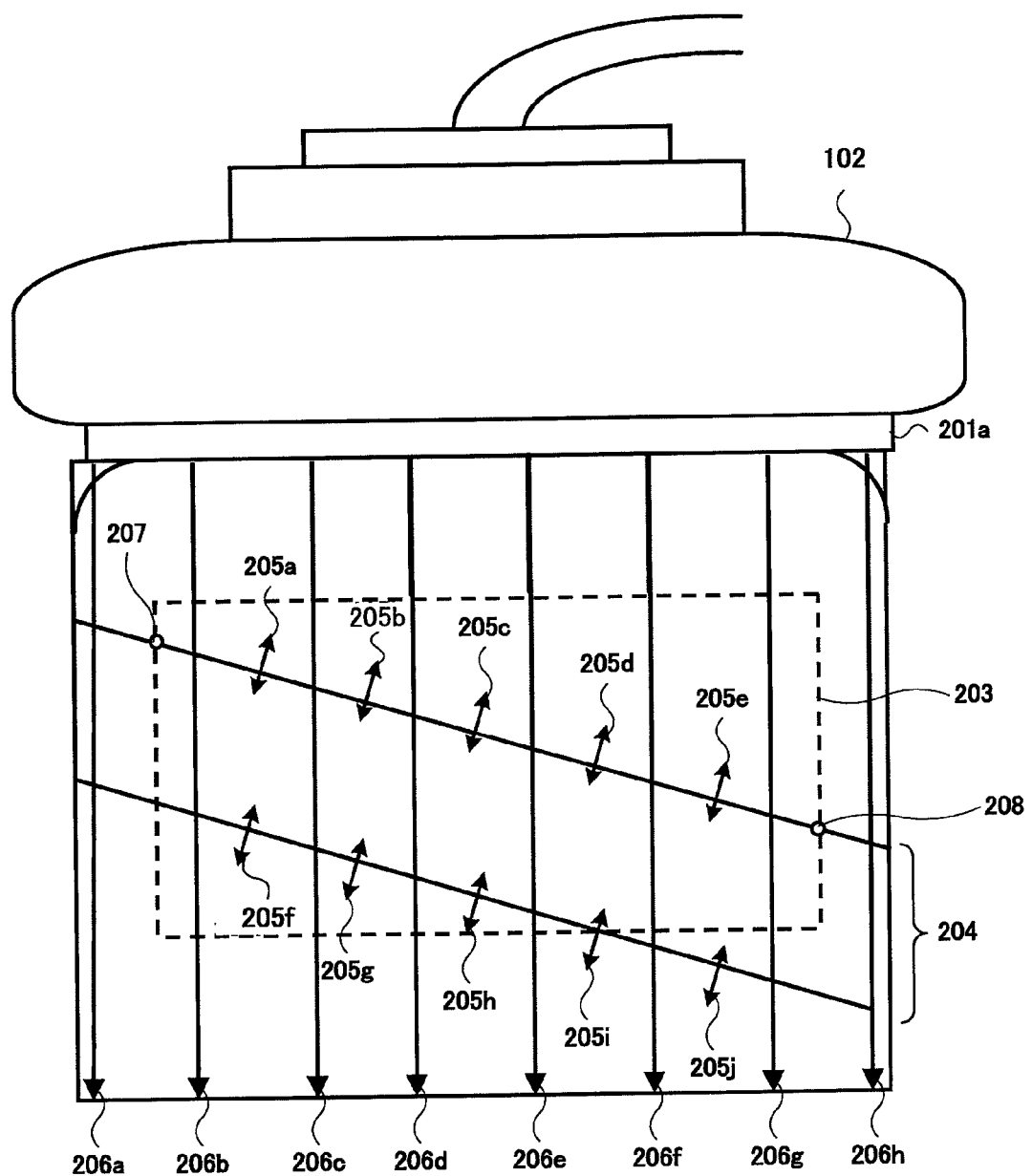
FIG. 3 is a diagram showing a form of an elasticity image when a displacement search direction is different from a tissue displacement direction.
Figure 4:
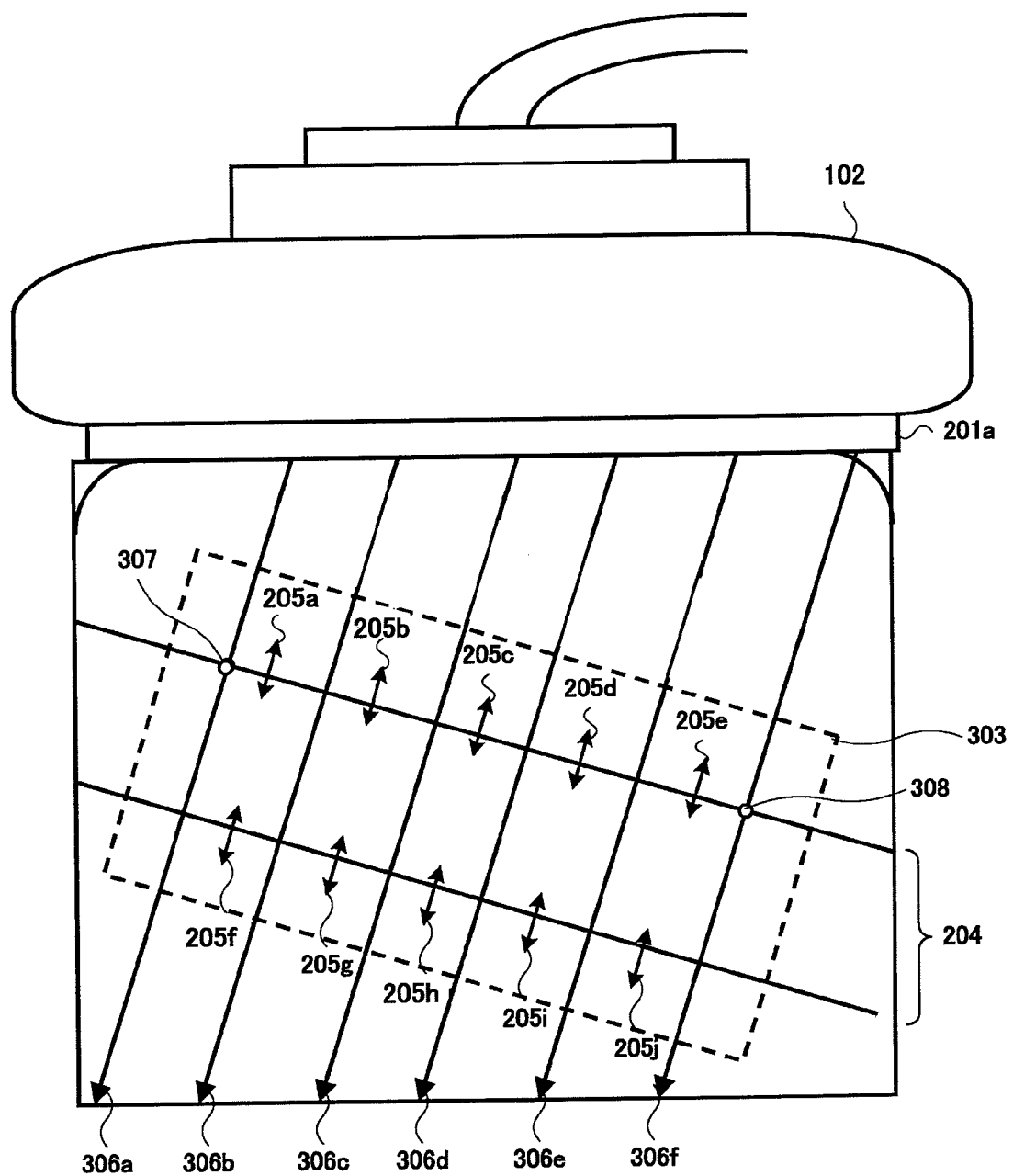
FIG. 4 is a diagram showing a form of an elasticity image when the displacement search direction matches the tissue displacement direction.

The first embodiment shows an example in which the tissue displacement direction is semi-automatically determined and ultrasound beams are deflected in the displacement search direction set to match the tissue displacement direction. FIG. 3 is a schematic diagram showing a form in which the displacement search direction does not match the tissue displacement direction. FIG. 4 is a schematic diagram showing a form in which the displacement search direction matches the tissue displacement direction.

Referring to FIG. 3, an ultrasound transmitting and receiving surface 201a of the probe 102 comes into contact with, e.g., the body surface of the subject 101. Herein, displacement search directions 206a to 206h are initialized in the ultrasound beam direction sent and received from/to the probe 102, that is, substantially in the vertical direction of the ultrasound transmitting and receiving surface 201a. Further, a vascular vessel (blood vessel) 204 in the subject 101 linearly exists with inclination to the ultrasound transmitting and receiving surface 201a. Furthermore, the region 203 of interest of the tissue for obtaining the elasticity image is set to be rectangle with parallel long portions to the ultrasound transmitting and receiving surface 201a, that is, to be oblong, as shown by a dotted line in the drawing. Incidentally, the region 203 of interest is set on the tomographic image displayed on the image display 112 in accordance with a command input via the operation unit 114.

In the form shown in FIG. 3, the peripheral tissue of the vascular vessel 204 is pressurized due to periodical pulsation of vascular vessel 204. The displacement of the tissue within the region 203 of interest from among the peripheral tissue is measured by the displacement calculating unit 105. Based on the measurement value of the displacement, the elasticity data is calculated by the strain calculating unit 106 and the modulus-of-elasticity calculating unit 107. Further, based on the calculation value of the elasticity data, the elasticity image is constructured by the color DSC 108.

However, in the example shown in FIG. 3, upon measuring the displacement of the tissue within the region 203 of interest, the displacement search directions 206a to 206h are ultrasound beam directions, i.e., short-side directions of the region 203 of interest. On the other hand, tissue displacement directions 205a to 205j due to the pulsation of the vascular vessel 204 are diameter directions of the vascular vessel 204. Therefore, the displacement search directions 206a to 206h intersects with the tissue displacement directions 205a to 205j with predetermined angles. That is, the displacement search direction 206a to 206h do not match the tissue displacement directions 205a to 205j. Upon measuring the displacement of the tissue in this state, there is a concern that the measurement value of the displacement includes an error due to the limit of calculating precision for correcting the displacement.

Then, according to the first embodiment, the angle of the region 203 of interest is semi-automatically corrected, thereby determining the displacement search direction to match the tissue displacement direction. Specifically, referring to FIG. 3, an operator determines reference points (hereinafter, referred to as intersection points 207 and 208) to two points at which short-side portions of the region 203 of interest intersects with the top end of the vascular vessel 204 via the operation unit 114 while viewing the tomographic image displayed on the image display 112. Incidentally, in place of the top end of the vascular vessel 204, the intersection point with the bottom end and the short-side portion may be determined. Further, the intersection points 207 and 208 may be set with the luminance of the tomographic image. In other words, the wall surface of the vascular vessel 204 on the screen of the image display 112 is displayed with high luminance. The control calculating unit 113 sets the intersection point of a high-luminance line formed on the wall surface of the vascular vessel 204 and the region 203 of interest as the intersection points 207 and 208 to use the luminance characteristics.

Referring to FIG. 4, after determining the intersection points 207 and 208, the detecting means 113C of the tissue displacement direction determines a direction orthogonal to a line section connecting the intersection points 207 and 208 as the tissue displacement direction. That is, according to the first embodiment, the intersection points 207 and 208 are determined, thereby semi-automatically detecting the tissue displacement direction.

Further, the angle correcting means 113E of the region of interest rotates and corrects the region 203 of interest so that the displacement between the direction orthogonal to the line connecting the intersection points 207 and 208 and the short-side direction of the region 203 of interest. In other words, the angle correcting means 113E of the region of interest resets a region 308 of interest so that the short-side direction matches the direction orthogonal to the line connecting the intersection points 207 and 208. Subsequently, the setting means 113B of the displacement search direction corrects the displacement search directions 206a to 206h to match the short-side direction of the region 308 of interest, thereby determining new displacement search direction 306a to 306f. The ultrasound transmitting and receiving unit 103 deflects the ultrasound beams along the displacement search directions 306a to 306f. Further, the displacement calculating unit 105 measures the displacement of the tissue in the displacement search directions 306a to 306f on the basis of received signals aligned in the displacement search directions 306a to 306f.

Figure 5:
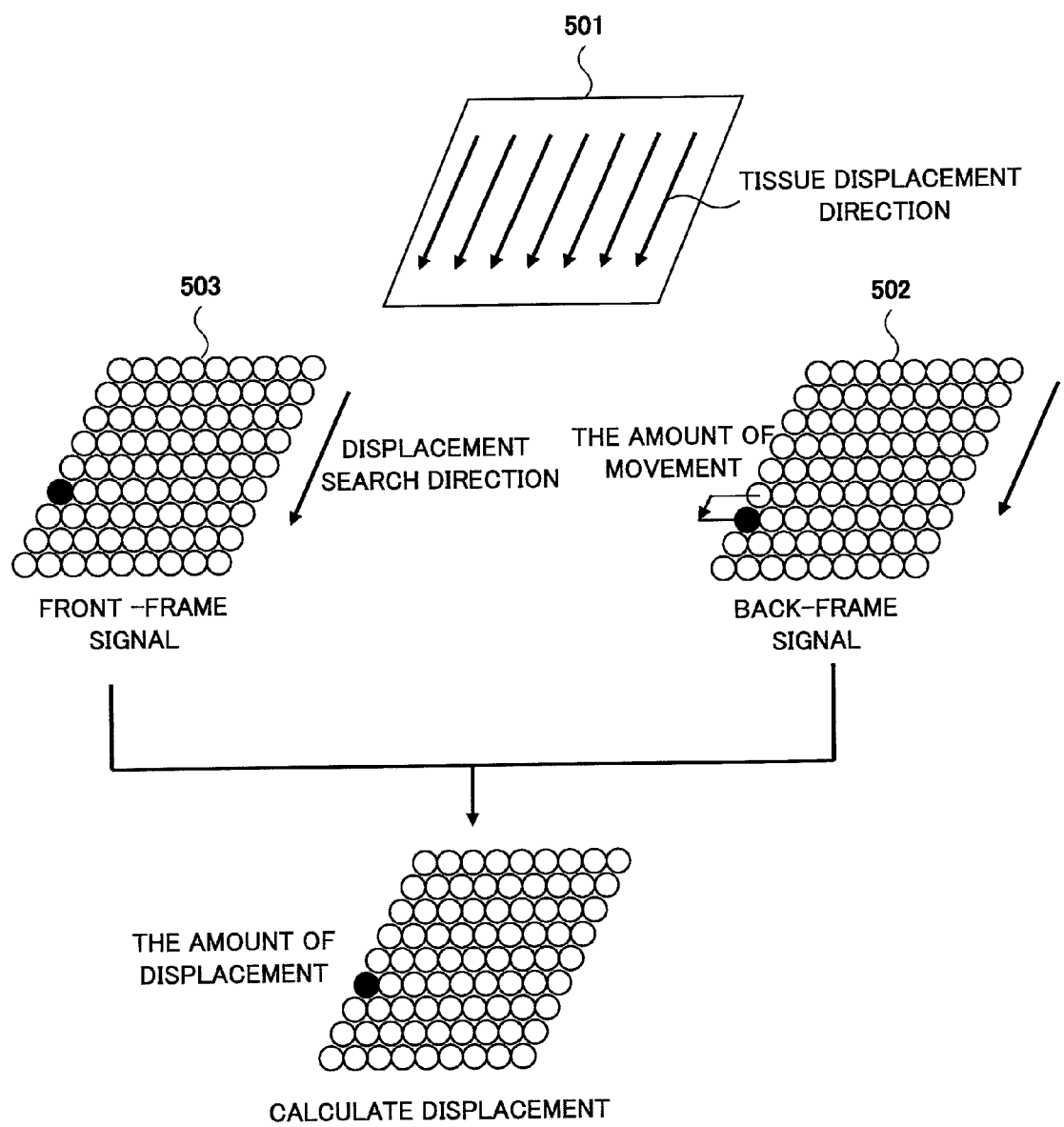
FIG. 5 is a diagram showing processing for calculating the displacement of a search direction.

FIG. 5 is a diagram showing an example for measuring the displacement of the tissue when the displacement search direction matches the tissue displacement direction. A region 501 of interest shown in FIG. 5 is a parallelogram obtained by correcting an angle of the original region of interest by the angle correcting means 113E of the region of interest. Herein, the tissue displacement direction is a direction along the inclination side of the region 501 of interest, i.e., a direction shown within the region 501 of interest by an arrow in the drawing. The setting means 113B of the displacement search direction resets the displacement search direction to a direction along the inclination side of the region 501 of interest. In brief, herein, within the region 501 of interest, the displacement search direction matches the tissue displacement direction.

First, the ultrasound transmitting and receiving unit 103 transmits and receives ultrasound beams via the probe 102 in the displacement search direction, thereby obtaining the received signals on time series. Subsequently, the displacement calculating unit 105 selects, as the first data, the currently-obtained RF signal frame data (N) 502. Herein, the RF signal frame data (N) 502 corresponds to signals aligned in the inclination direction of the side of the region 501 of interest, i.e., in the displacement search direction. The displacement calculating unit 105 also selects RF signal frame data (X) 503 that was obtained. Herein, the RF signal frame data (X) 503 also corresponds to signals in the inclination direction of the side of the region 501 of interest, i.e., in the displacement search direction. Further, the displacement calculating unit 105 executes correlation processing of the RF signal frame data (N) 502 and the RF signal frame data (X) 503, thereby measuring the amount of movement, i.e., the amount of displacement of the tissue in the displacement search direction.

According to the first embodiment, representatively shown in FIGS. 2 and 3, when the displacement search directions 206a to 206h do not match the tissue displacement directions 205a to 205j, the displacement search directions 306a to 306f are reset to match the tissue displacement directions 205a to 205j. Therefore, the displacement of the tissue in each of the displacement search directions 306a to 306f is measured, thereby measuring the displacement in the direction for actually displacing the tissue. Therefore, the precision of the measurement value of the displacement is improved. The elasticity image is constructed on the basis of the measurement value, thereby reducing artifact caused in the elasticity image. As a consequence, irrespective of the direction for pressurizing the tissue and the shape of the surface for pressurizing the tissue, the elasticity image is obtained with high quality for precisely indicating the characteristics such as the strain and hardness of the tissue.

For example, it is well known that the peripheral tissue is strained due to the pulsation of carotid artery at the thyroid portion. Therefore, upon imaging the elasticity image of the thyroid portion, the displacement of the peripheral tissue having the strain due to the pulsation of the carotid artery is measured and the elasticity image is constructed on the basis of the measurement value of the displacement. However, for example, the carotid artery is inclined to the ultrasound transmitting and receiving surface of the probe 102, the displacement search direction cannot match the tissue displacement direction. In this view point, according to the first embodiment, the displacement search direction matches the tissue displacement direction, thereby improving the measurement precision of the displacement of the tissue. Therefore, advantageous clinical data can be obtained.

FIG. 6 is a diagram showing examples of a setting state of the region of interest in various vascular vessels. FIGS. 6(A) and 6(C) show forms in which the vascular vessel is inclined to the ultrasound transmitting and receiving surface. The region of interest (ROI) in this case is set so that the short-side direction thereof is set to be vertical to the long direction of the vascular vessel. Further, the short-side direction of the region of interest, i.e., the displacement search direction is set to match the tissue displacement direction. That is, the displacement search direction matches the tissue displacement direction. Incidentally, in the example shown in FIG. 6(C), the vascular vessel is inclined in the direction inverse to the vascular vessel shown in FIG. 6(A). Therefore, the region of interest is rotated and corrected in the direction inverse to the case shown in FIG. 6(A) and, as a consequence, the displacement search direction matches the tissue displacement direction. FIG. 6(B) shows a form in which the vascular vessel exists in parallel with the ultrasound transmitting and receiving surface. In this case, the short-side direction of the region of interest, i.e., the displacement search direction matches the tissue displacement direction and the angle correction of the region of interest is not necessary.

Further, FIG. 6(D) shows a form in which the vascular vessel exists to be bent to the ultrasound transmitting and receiving surface. In this case, the region of interest is set to be fan-shaped with an arc corresponding to the curvature of the bent portion of the vascular vessel. The setting means 113B of the displacement search direction resets a direction vertical to a tangent line of arc of the region of interest as the displacement search direction. The ultrasound transmitting and receiving unit 103 transmits and receives ultrasound beams while gradually changing the ultrasound beam direction in accordance with the arc of the region of interest. Thus, even when the vascular vessel exists to be bent to the ultrasound transmitting and receiving surface, the displacement search direction can match the change in tissue displacement direction due to the bending of vascular vessel.

The fan-shaped region of interest is created by connecting a plurality of minute rectangular regions of interest. For example, as shown on the right side drawing in FIG. 6(D), with the same method as those shown in FIGS. 2, 3, and 6(A) to 6(C), the short-side directions of three minute rectangular regions of interest ROI 1 to ROI 3 match the tangent lines of the vascular vessel and the long-side direction matches a direction vertical to the tangent line of the vascular vessel, thereby dividing minute rectangular regions of interest ROI 1 to ROI 3 along the vascular vessel and a plurality of regions of interest. As mentioned above, a plurality of minute rectangular regions of interest are set throughout the whole the fan-shaped region of interest. Incidentally, the minute rectangular regions of interest are set within a range for ignoring the shape of the curvature of the vascular vessel.

Then, the displacement search direction is set to match the long-side directions of the minute rectangular regions of interest ROI 1, ROI 2, and ROI 3, i.e., the tissue displacement direction. As a consequence, at the minute rectangular region of interest, the displacement search direction can match the tissue displacement direction. In other words, the displacement search direction can match the tissue displacement direction throughout the whole fan-shaped region of interest. With the setting method of the region of interest, the shape of the vascular vessel is not limited to be fan-shaped and can be complicated-shaped.

In the examples, the pulsation of the vascular vessel 204 is a pressure source and the elasticity image of the tissue with pressurization of the pulsation of the vascular vessel 204 is obtained. However, the present invention is not limited to this. For example, the present invention can be also applied to a form for manually pressing and pressurizing the probe 102 that comes into contact with the body surface of the subject 101 and a form for pressurizing the probe 102 by the transducer that comes into contact with the body surface of the subject 101. In brief, when the displacement search direction does not match the tissue displacement direction, the present invention may be applied.

Second Embodiment

The second embodiment is different from the first embodiment in which the ultrasound beams are deflected in that the elasticity calculating direction predetermined within the region of interest, i.e., only the displacement search direction within the region of interest matches the tissue displacement direction when the displacement search direction matches the tissue displacement direction. Therefore, the different points will be mainly described.

Figure 7:
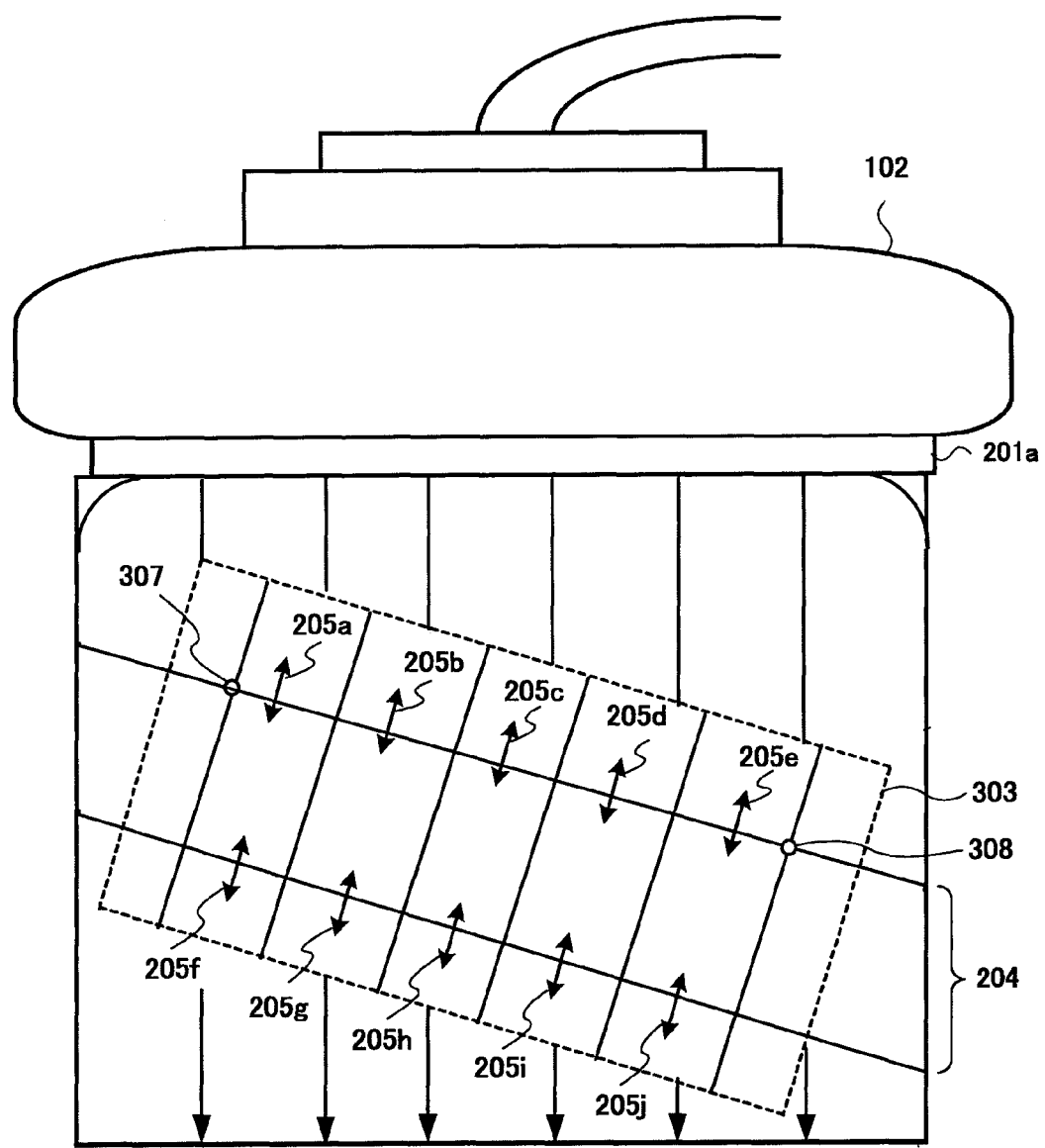
FIG. 7 is a diagram showing one processing for automatically detecting the tissue displacement direction.

FIG. 7 is a diagram for illustrating the operation of the setting means 113B of the displacement search direction according to the second embodiment. An example shown in FIG. 7 is different from that shown in FIG. 4 in that the emission direction of ultrasound beams is vertical to an ultrasound transmitting and receiving surface 201a.

Upon imaging the elasticity image of the tissue of the subject 101, the ultrasound transmitting and receiving unit 103 first transmits and receives the ultrasound beams in the vertical direction of the ultrasound transmitting and receiving surface 201a, thereby obtaining the signal of the subject 101. Herein, the setting means 113B of the displacement search direction according to the second embodiment sets the displacement search direction that is preset to the region 303 of interest to the tissue displacement directions 205a to 205j. Further, the setting means 113B of the displacement search direction outputs a command for selecting signals aligned in the displacement search direction after the correction from among the signals output from the ultrasound transmitting and receiving unit 103 and a command for measuring the displacement of the tissue in the displacement search direction on the basis of the selected signals to the displacement calculating unit 105.

That is, signals corresponding to the tissue displacement directions 205a to 205j are selected from the output signals from the ultrasound transmitting and receiving unit 103 and the elasticity calculation is executed. As a consequence, only the displacement search direction within the region 303 of interest matches the tissue displacement direction. Therefore, according to the second embodiment, when the displacement search direction matches the tissue displacement direction, the displacement search direction can match the tissue displacement direction within the region 303 of interest without deflecting the ultrasound beams. Thus, in addition to the first embodiment, it is easy that the displacement search direction matches the tissue displacement direction in accordance with the complicated movement of the tissue.

Third Embodiment

The third embodiment is different from the first embodiment with the structure for automatically detecting the tissue displacement direction in that the tissue displacement direction is automatically detected. Therefore, the different points will be mainly described.

Figure 8:
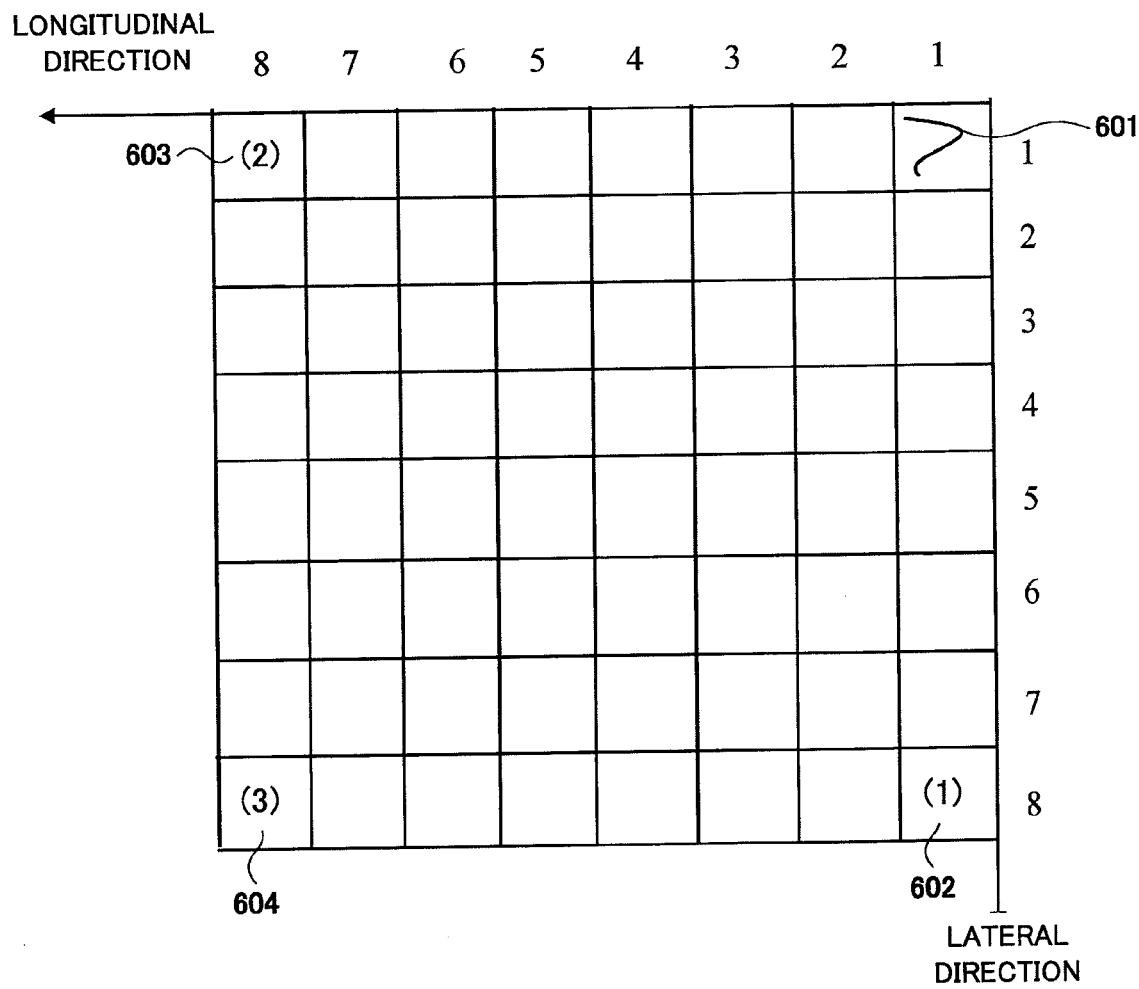
FIG. 8 is a diagram showing a form for imaging an elasticity image when the displacement search direction set to the region of interest matches the tissue displacement direction.

FIG. 8 is a conceptual diagram showing an example of the operation of the detecting means 113C of the tissue displacement direction shown in FIG. 2. The abscissa in FIG. 8 denotes the coordinate of the subject substantially in parallel with the ultrasound transmitting and receiving surface 201a, and the ordinate denotes the coordinate of the subject substantially in the vertical direction of the ultrasound transmitting and receiving surface 201a. The units of the abscissa and the ordinate are millimeter (mm).

Referring to FIG. 8, the detecting means 113C of the tissue displacement direction executes the correlation calculation of the tomographic images after/before applying pressure to the tissue within a wide range on the basis of signals corresponding to pixels. Specifically, the detecting means 113C obtains a signal 601 before applying pressure to the tissue. Herein, the signal 601 is at the position of 1 [mm] in the longitudinal direction and of 1 [mm] in the lateral direction. Further, the detecting means 113C detects the moving destination of the signal 601 upon applying the pressure to the tissue with the correlation processing, and determines the tissue displacement direction on the basis of the detection result.

For example, upon detecting the moving destination of the signal 601 as the position of a signal 602 (8 [mm] in the longitudinal direction and 1 [mm] in the lateral direction), upon detecting the moving destination of the signal 601 at the position of the signal 602, the detecting means 113C determines that the tissue displacement direction is in the longitudinal direction (e.g., 0 degree). Further, upon detecting the moving destination of the signal 601 at the position of a signal 603 (1 [mm] in the longitudinal direction and 8 [mm] in the lateral direction), the detecting means 113C determines that the tissue displacement direction is in the lateral direction (e.g., 90 degrees). Furthermore, upon detecting the moving destination of the signal 601 at the position of a signal 604 (8 [mm] in the long-side direction and 8 [mm] in the lateral direction), the detecting means 113C determines that the tissue displacement direction is in the oblique direction (e.g., 45 degrees). The detecting means 113C executes detecting processing of the tissue displacement direction every coordinate and detects an average of the detection values of the coordinates as the tissue displacement direction. The tissue displacement direction is output to the setting means 113B of the displacement search direction and the angle correcting means 113E of the region of interest. Incidentally, processing for measuring the displacement of the tissue so that the displacement search direction matches the tissue displacement direction is similar to that according to the first embodiment.

That is, upon imaging the elasticity image of the thyroid, even if pressure is applied to the tissue such as the thyroid, the tissue can be displaced in the lateral direction. Then, the tissue displacement direction cannot be grasped. On the other hand, according to the third embodiment, since the tissue displacement direction is automatically, objectively, and quantitatively detected, the measurement precision of the displacement of the tissue can be improved.

Fourth Embodiment

The fourth embodiment is different from the third embodiment in that the direction of the blood vessel is used upon automatically detecting the tissue displacement direction. Therefore, different points will be mainly described.

An ultrasound diagnostic apparatus according to the fourth embodiment has a Doppler image reconstructing unit 900, as shown in FIG. 1. The Doppler reconstructing unit 900 calculates the Doppler deviation on the basis of received signals on time series, captured from the ultrasound transmitting and receiving unit 103, and constructures a Doppler image (e.g., color blood flow image) from the Doppler deviation. Further, the setting means 113B of the displacement search direction according to the fourth embodiment determines the displacement search direction that matches the tissue displacement direction, on the basis of the direction of blood flow that can be determined by the Doppler image reconstructing unit 900.

FIG. 9 is a diagram for illustrating the operation of the setting means 113B of the displacement search direction according to the fourth embodiment. First, FIG. 9A is a diagram showing a color blood flow image that is superimposed to the vascular vessel 204 shown in FIG. 3 and the resultant image is displayed. Herein, the color blood flow image is output to the image display 112 via the image combining unit 111 from the Doppler image reconstructing unit 900.

FIG. 9B is a schematic diagram showing an example for setting the displacement search direction to match the tissue displacement direction on the basis of the blood vessel direction. The detecting means 113C of tissue displacement direction detects the direction of blood flow on the basis of the color blood vessel image shown in FIG. 9A, and determines the direction orthogonal to the direction of blood flow as the tissue displacement direction. The setting means 113B of the displacement search direction determines the displacement search direction to match the tissue displacement direction determined by the detecting means 113C. Incidentally, the setting processing or rotating and correcting processing of the region of interest 303 and the processing for deflecting the ultrasound beam direction in accordance with the displacement search direction are similar to those according to the first embodiment. As described according to the second embodiment, processing for the displacement search direction of the region of interest 303 to match the tissue displacement direction may be applied.

According to the fourth embodiment, since the tissue displacement direction is automatically determined on the basis of the direction of blood flow that can be detected from the Doppler blood flow image, operation for matching the tissue displacement direction to the displacement search direction becomes easy. For example, even if the subject 101 has the blood vessel that is bent, the displacement search direction can be easily determined on the basis of the Doppler blood flow image of the blood vessel.

Fifth Embodiment

The fifth embodiment is different from the first embodiment having the structure for deflecting the ultrasound beams received/sent by the probe 102 in that the inclination of the probe 102 is manually adjusted upon matching the displacement search direction to the tissue displacement direction. Therefore, different points will be mainly described.

The inclination of the probe 102 is changed, thereby changing the inclination angle of the ultrasound transmitting and receiving surface 201a of the probe 102. Therefore, it is possible to adjust the direction of the ultrasound beams received/sent by the ultrasound transmitting and receiving surface 201a. That is, upon the displacement search direction as the direction of the ultrasound beams, the inclination of the probe 102 is adjusted, thereby matching the displacement search direction to the tissue displacement direction.

However, the inclination of the probe 102 is adjusted on the basis of the experience and instinct and operation for matching the displacement search direction to the tissue displacement direction is thus complicated. Then, the guide information creating means 113F shown in FIG. 2 creates guide information indicating the inclination direction and the inclination angle of the probe 102 when the displacement search direction matches the tissue displacement direction and allows the image display 112 to display the created information.

Figure 10:
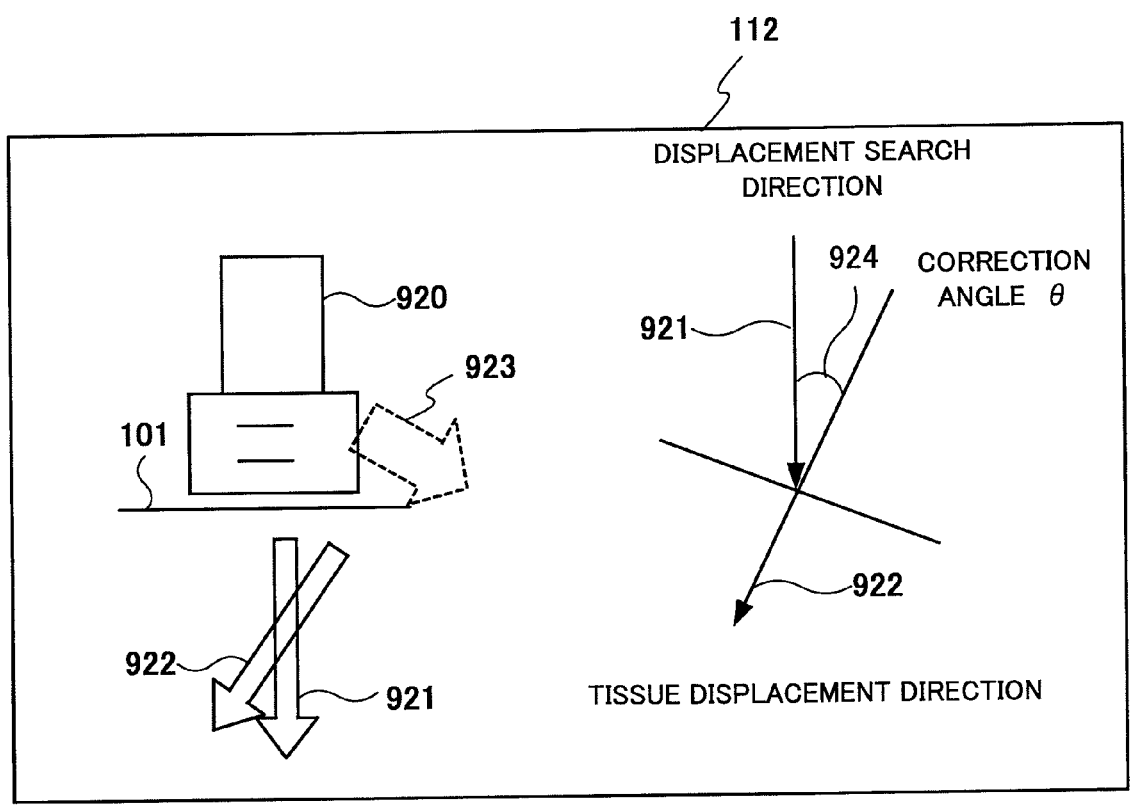
FIG. 10 is a diagram showing a display example of guide information indicating an inclination direction and an inclination angle of an ultrasound probe.

FIG. 10 is a display example of the guide information indicating the inclination direction and the inclination angle of the probe 102. Incidentally, a positional sensor for detecting the position and the inclination of the probe 102 in real time is arranged. Referring to FIG. 10, the guide information creating means 113F creates and displays a model image 920 of the probe 102 that comes into contact with the body surface of the subject 101, an arrow image 921 indicating the displacement search direction set to match the ultrasound beam direction of the probe 102, an arrow image 922 indicating the tissue displacement direction of the tissue of the subject 101, and a guide image 923 indicating the inclination direction of the probe 102 indicating the inclination direction when the displacement search direction matches the tissue displacement direction. Further, the guide information creating means 113F may angle information 924 indicating a correction angle θ corresponding to the deviation between the displacement search direction and the tissue displacement direction. Herein, the correction angle θ is guide information indicating the inclination angle of the probe 102.

According to the fifth embodiment, the guide information such as the guide image 923 and angle information 924 becomes an objective and quantitative index for supporting the operation for matching the displacement search direction to the tissue displacement direction by adjusting the inclination of the probe 102. Therefore, the operator can visually grasp an inclination direction of the target of the probe 102, thereby precisely and simply performing the operation for matching the displacement search direction to the tissue displacement direction. As a consequence, the measurement precision of the displacement of the tissue is improved and the convenience of the apparatus can be improved.

Figure 11:
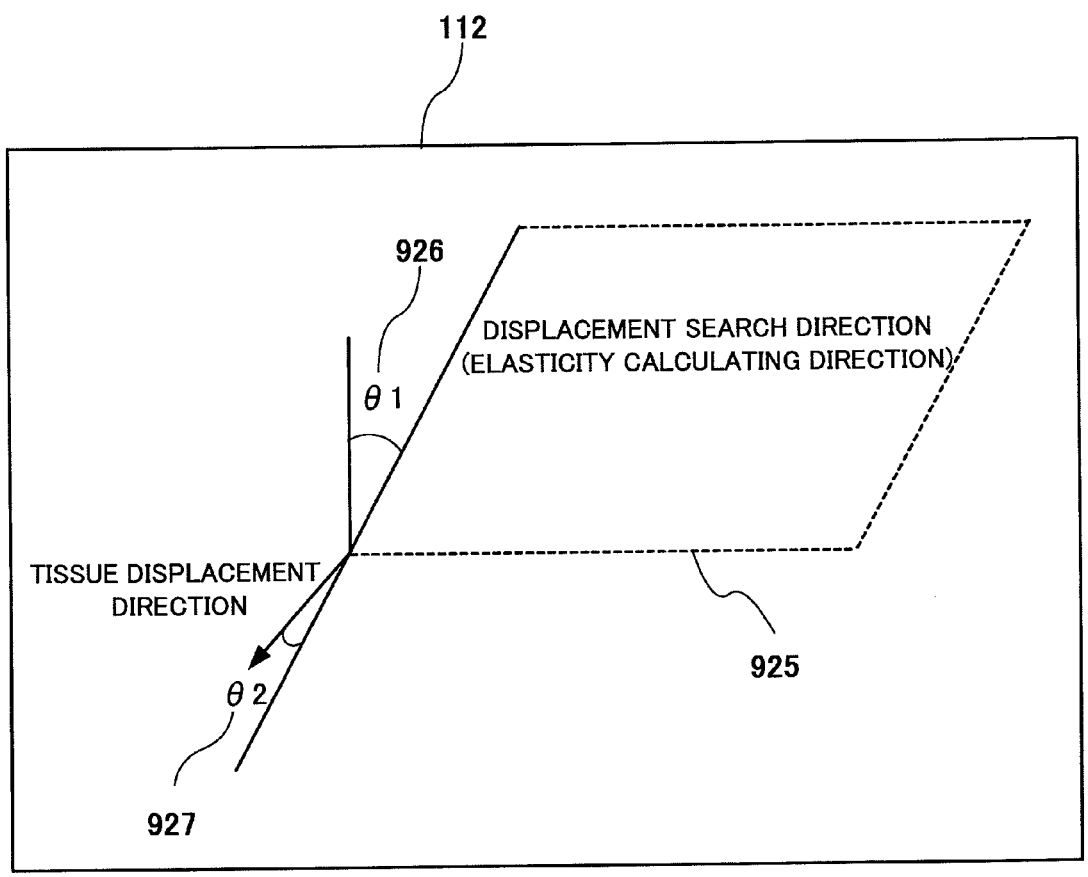
FIG. 11 is a diagram showing a form of displaying guide information indicating angle information arranged at the region of interest.

Referring to FIG. 11, the guide information creating means 113F may align and display, on the region of interest 925, angle information 926 indicating an angle $\theta_1$ formed between the displacement search direction and the vertical direction (e.g., depth direction of the subject 101), and angle information 927 indicating an angle $\theta_2$ formed between the displacement search direction and the tissue displacement direction. As a consequence, the operator can relatively and visually grasp the displacement search direction and the tissue displacement direction of the region of interest 925 of the subject 101.

As mentioned above, according to the embodiments, irrespectively of the direction for pressurizing the tissue and the shape of a surface for pressurizing the tissue, it is possible to easily obtain the elasticity image with high quality, precisely indicating the characteristics such as the strain and hardness of the tissue.

As shown in FIGS. 1 and 2, the control functions necessary for ultrasonogram imaging according to the embodiments are described on the unit basis of block. The control functions can be collected as an ultrasonogram imaging program and the ultrasonogram imaging program can be executed by a control computer. For example, the ultrasonogram imaging program enables a control computer to execute: a setting sequence of setting a displacement search direction to match the tissue displacement direction of the tissue of the subject 101; a sequence of supplying a transmitting drive signal to the probe 102 that receives and transmits ultrasound waves to/from the subject 101; a sequence of processing a received signal output from the probe 102; a sequence of measuring the displacement of the search direction from signals after the receiving processing; a sequence of reconstructing the elasticity image on the basis of the measurement value of the displacement; and a sequence of displaying the elasticity image.

As mentioned above, the ultrasound diagnostic apparatus according to the embodiments of the present invention is described. The ultrasound diagnostic apparatus according to the present invention can be variously embodied without departing the essentials and main features of the present invention. Therefore, the embodiment is an example and is not limited to this. That is, the range of the present invention includes the modification and change of the equivalent range.

The invention claimed is:

1. An ultrasound diagnostic apparatus comprising:
an ultrasound probe for transmitting and receiving ultrasound waves to/from a subject; transmitting means for supplying a drive signal to the ultrasound probe transmitting ultrasound waves to the subject; receiving means for receiving and processing a received signal output from the ultrasound probe; reconstructing means for reconstructing an elasticity-image on the basis of displacement of a tissue measured from an output signal from the receiving means; and displaying means for displaying the elasticity image; wherein the apparatus further comprises;
a tissue displacement direction detecting means for detecting the tissue displacement direction; and
displacement search direction setting means for deflecting ultrasound beams to align with the detected tissue displacement direction; wherein
the reconstructing means measures the tissue displacement in the deflected ultrasound beam direction and reconstructs the elasticity image.

2. The ultrasound diagnostic apparatus according to claim 1, further comprising:
region setting means for setting a region of interest with a predetermined displacement search direction; and
correcting means for correcting a rotation angle of the region of interest so that the search direction matches to the tissue displacement direction, wherein
the displacement search direction setting means outputs, to the transmitting means or the receiving means, a command for deflecting the ultrasound beam to match the search direction of the region of interest after the rotation and correction.

3. The ultrasound diagnostic apparatus according to claim 2, wherein the region setting means sets a rectangular- or fan-shaped region of interest corresponding to the tissue of the subject.

4. The ultrasound diagnostic apparatus according to claim 1, wherein the displacement search direction setting means outputs, to the elasticity-image reconstructing means, a command for selecting signals aligned in the search direction and a command for calculating the displacement of the search direction on the basis of the selected signals, from among signals output from the receiving means.

5. The ultrasound diagnostic apparatus according to claim 1, further comprising:
region setting means for setting a region of interest with a predetermined displacement search direction; and
correcting means for correcting a rotation angle of the region of interest so that the search direction matches to the tissue displacement direction, wherein
the displacement search direction setting means outputs, to the elasticity-image reconstructing means, a command for selecting signals aligned corresponding to the search direction of the region of interest from among signals output from the receiving means and corrected by the correcting means, and a command for calculating the displacement of the search direction on the basis of the selected signals.

6. The ultrasound diagnostic apparatus according to claim 5, wherein the region setting means sets a rectangular- or fan-shaped region of interest corresponding to the tissue of the subject.

7. The ultrasound diagnostic apparatus according to claim 1, wherein the displacement search direction setting means divides the region of interest set to the tissue into a plurality of minute rectangular regions of interest, specifies the tissue displacement direction of the minute rectangular regions of interest, and sets the search direction to match the tissue displacement direction.

8. The ultrasound diagnostic apparatus according to claim 1, wherein
the tissue displacement direction detecting means determines, as the tissue displacement direction, a direction orthogonal to a line segment between two reference points determined on a tomographic image of the tissue.

9. The ultrasound diagnostic apparatus according to claim 1, wherein
the tissue displacement direction detecting means executes correlation process of a tomographic image before applying pressure to a tissue and a tomographic image during applying pressure to the tissue, obtains a moving direction of a portion on the tomographic image, and determines the moving direction as the tissue displacement direction.

10. The ultrasound diagnostic apparatus according to claim 1, wherein
the tissue displacement direction detecting means obtains a direction of blood flow from the output signal from the receiving means with Doppler calculating processing, and determines a direction orthogonal to the direction of blood flow as the tissue displacement direction.

11. The ultrasound diagnostic apparatus according to claim 1, wherein the displaying means displays guide information indicating an inclination direction or an inclination angle of the ultrasound probe in order to align the ultrasound beams with the tissue displacement direction, upon setting the search direction to the direction of ultrasound beam of the ultrasound probe.

12. The ultrasound diagnostic apparatus according to claim 1, wherein the displaying means displays at least one of an arrow image indicating the tissue displacement direction, an arrow image indicating the displacement search direction, and an arrow image of the ultrasound probe in the direction of the ultrasound beam.

13. The ultrasound diagnostic apparatus according to claim 1, wherein the displaying means displays an angle formed between the tissue displacement direction and the displacement search direction.

14. A non-transitory computer readable medium containing a program which when executed on a computer causes the computer to take an ultrasonogram by performing steps comprising:
a supplying process for supplying a drive signal to an ultrasound probe that transmits the ultrasound waves to a subject;
a receiving process for receiving and processing a signal output from the ultrasound probe;
a detecting process of a tissue displacement direction for detecting the tissue displacement direction;
a setting process of a displacement search direction for deflecting ultrasound beams to align with the detected tissue displacement direction;
a measuring process for measuring the tissue displacement in the deflected ultrasound beam direction;
a reconstructing process for reconstructing an elasticity image on the basis of the measurement value of the displacement; and
a displaying process for displaying the elasticity image.

15. A method for imaging an ultrasonogram comprising:
a transmitting step for supplying a drive signal to an ultrasound probe that transmits and receives ultrasound waves to/from a subject;
a receiving step for receiving and processing a signal output from the ultrasound probe;
a detecting step of a tissue displacement direction for detecting the tissue displacement direction;
a setting step of a displacement search direction for deflecting ultrasound beams to align with the detected tissue displacement direction;
a measuring step for measuring the tissue displacement in the deflected ultrasound beam direction;
a reconstructing step for reconstructing an elasticity image on the basis of the measurement value of the displacement; and
a displaying step for displaying the elasticity image.

16. A method for imaging an ultrasonogram according to claim 15, wherein the setting step of the displacement search direction comprises:
a step of selecting signals aligned corresponding to the search direction from among signal output from the receiving means; and
a step of calculating the displacement of the search direction on the basis of the selected signal.

17. A method for imaging an ultrasonogram according to claim 15, wherein the setting step of the displacement search direction comprises:
a step of dividing the region of interest set to the tissue into a plurality of fine and rectangular regions of interest, specifying the tissue displacement direction of the fine and rectangular region of interest, and setting the search direction to match the tissue displacement direction.

18. A method for imaging an ultrasonogram according to claim 15,
wherein the detecting step of the tissue displacement direction comprises a step of determining, as the tissue displacement direction, a direction orthogonal to a line segment between two reference points determined on a tomographic image of the tissue.

19. A method for imaging an ultrasonogram according to claim 15,
wherein the detecting step of the tissue displacement direction comprises a step of executing correlation processing of a tomographic image before applying pressure to the tissue and a tomographic image during applying pressure to the tissue, obtaining a moving direction of a portion on the tomographic image, and determining the moving direction as the tissue displacement direction.

20. A method for imaging an ultrasonogram according to claim 15,
wherein the detecting step of the tissue displacement direction comprises a step of allowing a direction of blood flow to be obtained from the output signal from the receiving means with Doppler calculating processing, and determining a direction orthogonal to the direction of blood flow as the tissue displacement direction.

21. A method for imaging an ultrasonogram according to claim 15, wherein the display step comprises a step of displaying guide information indicating an inclination direction or an inclination angle of the ultrasound probe in order to align the ultrasound beams with the tissue displacement direction, upon setting the search direction to the direction of ultrasound beam of the ultrasound probe.

22. A method for imaging an ultrasonogram according to claim 15, wherein the display step includes a step of displaying at least one of an arrow image indicating the tissue displacement direction, an arrow image indicating the displacement search direction, and an arrow image of the ultrasound probe in the direction of the ultrasound beam.

23. A method for imaging an ultrasonogram according to claim 15, wherein the displaying step comprises a step of displaying an angle formed between the tissue displacement direction and the displacement search direction.

* * * * *